United States Patent [19]
Simkins et al.

[11] Patent Number: 5,523,742
[45] Date of Patent: Jun. 4, 1996

[54] MOTION SENSOR

[75] Inventors: Thomas E. Simkins, Troy; Mark A. Johnson, Rensselaer, both of N.Y.

[73] Assignee: The United States of America as represented by the Secretary of the Army, Washington, D.C.

[21] Appl. No.: 443,911

[22] Filed: May 18, 1995

Related U.S. Application Data

[63] Continuation-in-part of Ser. No. 312,853, Sep. 23, 1994, abandoned, which is a continuation of Ser. No. 154,324, Nov. 18, 1993, abandoned.

[51] Int. Cl.$^6$ ..................................................... G08B 23/00
[52] U.S. Cl. ........................... 340/573; 340/566; 340/693; 128/782; 200/61.45 R
[58] Field of Search ........................................ 340/573, 566, 340/686, 687, 689, 693; 128/721, 782; 200/61.45 R, 61.52

[56] References Cited

U.S. PATENT DOCUMENTS

| | | | |
|---|---|---|---|
| 3,553,399 | 1/1971 | Osen | 200/61.45 R |
| 3,796,208 | 3/1974 | Bloice | 628/653.1 |
| 4,322,714 | 3/1982 | Morgan | 340/566 |
| 4,337,402 | 6/1982 | Nowakowski | 200/61.45 R |
| 4,536,755 | 8/1985 | Holzgang et al. | 200/61.52 |
| 4,747,216 | 5/1988 | Kelly et al. | 340/689 |
| 4,833,456 | 5/1989 | Heller | 340/571 |
| 4,884,067 | 11/1989 | Nordholm et al. | 340/686 |

*Primary Examiner*—Brent A. Swarthout
*Assistant Examiner*—Benjamin C. Lee
*Attorney, Agent, or Firm*—Saul Elbaum; Edward Goldberg; Michael C. Sachs

[57] ABSTRACT

A motion detection device for use as a monitor for patient movement, including a sensor for generating motion signals, an integrator for integrating the motion signals over a period of time, and a threshold level of signals generating an alarm signal upon exceeding a predetermined minimum value of the motion signals to activate an alarm. The sensor includes an edge detector for providing a motion sensed outpost of a series of sharp voltage rises and falls to generate a sequence of voltage pulses of predetermined magnitude and time duration which generate an alarm signal if the pulses are generated faster than a preset rate of voltage decay based upon a preselected minimum movement to be sensed. The preferred intermittent switch comprises a conductive rolling sphere in a cylindrical chamber having a conductive wall with one electrical pole and end plates electrically insulated from the conductive wall and having the other electrical pole such that movement of the element caused by movement of the cylinder will generate intermittent electrical contact between one end plate and the cylinder wall. The device preferably further includes a transmitter producing a transmitted radio signal upon receipt of the alarm signal, the radio signal being receivable by a conventional radio.

5 Claims, 2 Drawing Sheets

EDGE DETECTOR & CONDITIONER

INTEGRATOR & LATCH

OSCILLATORS & TRANSMITTER

MOTION SENSOR

The invention described herein may be made, used, or licensed by or for the Government for Governmental purposes.

This application is a continuation in part of application Ser. No. 08/312,324, filed Sep. 23, 1994, now abandoned, which itself is a continuation of application Ser. No. 08/154,324, filed Nov. 18, 1993, now abandoned.

FIELD OF THE INVENTION

The present invention relates to a monitoring device for sleeping individuals. More particularly the present invention relates to a motion sensor which detects a particular type of motion over a preselected period of time to then trigger an alarm.

BACKGROUND OF THE INVENTION

Epilepsy is a disorder of the brain characterized by recurring seizures, in which there are uncontrolled electrical discharges of brain cells. Epilepsy may arise from a very small area of damaged brain tissue, or from the entire brain. There may be no apparent brain damage, or damage may be limited to an area so small it cannot be detected. Therefore, in nearly one-half the cases, the cause of epilepsy is unknown.

There are several types of seizures associated with epilepsy, the most common of which are generalized tonic-clonic (grand mal), absence (petit mal), complex partial (psychomotor), and elementary partial (focal motor). Each seizure type can be characterized by various symptoms. However, the seizures are generally not life threatening, lasting at most up to three minutes. The exception is status epilepticus, also called continuous seizure state. This is the occurrence of repetitive or continuous seizures and affects approximately 3 to 5% of those individuals suffering from epilepsy. It can exist with all types of seizures and may result in irreversible brain damage or death without prompt medical treatment.

One of the specific problems encountered by parents having children afflicted with epilepsy, particularly status epilepticus, is the problem of alerting the parents when the child may be having an epileptic seizure during sleeping hours. To date the only recourse the parents have is to sleep with the child, in the same bed, hoping to be awakened by the seizure during its early stages when the seizure motion may be quite mild. Often, the parents will choose to supplement this safeguard by using an alarm clock, set to sound every hour, to awaken and observe the state of the child. This, of course, places an extraordinary burden on both the child and the parents and is inherently unreliable. The intermittent sleep afforded the parents as well as the desire for privacy by the child and by the parents make the procedure impractical and inefficient.

Motion sensor devices are obvious solutions to the aforementioned problem, provided that such devices be designed to ignore the casual motions of a sleeping child (rolling over, etc.) while responding to those motions characteristic of a seizure, however mild at the beginning. Existing motion sensor devices such as accelerometers or displacement followers could conceivably be designed to detect certain types of motion while ignoring others, but are invariably expensive and, when the required signal conditioning equipment is included, form a bulky package. Moreover, these devices commonly require electrical connections between the transducer (affixed to the patient) and its associated equipment located near, but not on, the patient.

Accordingly, it is an object of this invention to provide a device for sensing the motion of concern while ignoring, for the most part, other non-harmful motion such as ordinary movement during sleep.

Yet another object of this invention is to provide a simple, effective device for monitoring epileptics without disturbing the sleep of the patient or the observer unless there is a need for concern.

Other Objects will appear hereinafter.

SUMMARY OF THE INVENTION

It has now been discovered that the above and other objects of the present invention may be accomplished in the following manner. Specifically, the invention comprises a motion detection device for use as a monitor for patient movement.

The device includes a sensor means suitable to be attached to a patient for generating motion signals in response to movement of the sensor means. The sensor means includes an intermittent switch means for generating a series of sharp voltage rises and falls to generate a sequence of voltage pulses of predetermined magnitude and time duration. Preferably the sensor means includes edge detector means for providing a motion sensed output. The edge detector means includes a pair of coupled NOR gages and a non-retriggerable monostable multivibrator to condition the motion signals to match the condition of the switch means.

The integrating means is adapted to integrate the motion signals over a period of time. Part of the integrating means is a threshold means for generating an alarm signal when a predetermined minimum value of the motion signal is exceeded. An intermittent switch is prodded for responding to the alarm signal and activating a alarm. A transmitter produces a transmitted radio signal upon receipt of the alarm signal. The radio signal is receivable by a conventional radio.

The integrating means includes a voltage leakage circuit for defining the minimum amount of movement needed to generate the alarm signal. The device further includes reset means for bringing the device to an at-rest condition. The device also includes means for adjusting the sensitivity of the threshold means.

The preferred intermittent switch comprises a conductive rolling sphere in a cylindrical chamber having a conductive wall with one electrical pole. End plates are electrically insulated from the conductive wall and from the other electrical pole so that movement of the sphere caused by movement of the cylinder will generate intermittent electrical contact between one end plate and the cylinder wall. This cylinder is easily attached to a patient for monitoring.

The present invention offers an extremely simple, lightweight and inexpensive means for detecting motion. Since the problem of the present invention is solved by detecting or sensing motion, there is no need, to measure it. Devices which measure motion involve considerable technical and cost overkill without adding anything to the desired objects and goals of this invention.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
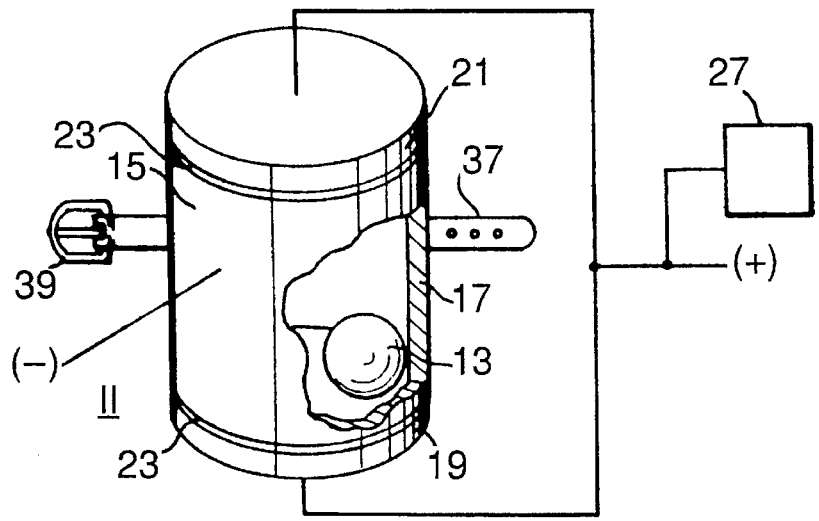
FIG. 1 is a schematic view illustrating the sensor of this invention, shown in perspective with parts broken away for clarity, with means for attachment to a patient.

As shown in the FIG. 1, the sensor 11 is a simple design in which a conductive rolling element or sphere 13 is placed in a conductive cylindrical chamber 15 having a conductive wall 17 with one electrical pole, shown in FIG. 1 as the negative pole. End plates 19 and 21 are electrically insulated by insulating layer 23 from the conductive wall 17 and have the other electrical pole, positive as shown in FIG. 1, such that movement of sphere 13 caused by movement of the cylinder will generate intermittent electrical contact between one end plate 19, for example, and the cylinder wall 17. Wrist watch strap 37 with an adjustable fastening device such as buckle 39 or, alternatively, a Velcro® fastener or clasp (not shown) allows attachment of the sensor or the entire monitor to the patient on the wrist, ankle, arm or leg. It also may be worn as a belt, depending upon particular size and comfort need of the patient.

This sensor 11 effectively operates as a 'jiggle' switch as the small, electrically conductive sphere 13 is able to move freely inside the small hollow cylinder 15. Wall 17 is conductive as are end plates 19 and 21, each of which are separated from wall 17 by an insulator 23. The end plates 19 and 21 are electrically connected and form one pole of the switch.

When sphere 13 is in contact with either end plates 19 or 21 and with the cylinder wall 17, the switch is (electrically) closed through such mechanical positioning, hereafter referred to as mechanically closed. Depending on the presence of oxides and/or surface roughness, the contact resistance varies and may be quite high such that the switch may or may not be electrically closed. The important feature is that even small motions of the switch cause the ball 13 to roll. Because this mechanically closed switch position is the only stable position for the ball 13 in cylinder 15. i.e., in contact with wall 17 and end plate 19 or 21, most of the rolling takes place In this configuration. Ideally the inside cylinder walls, and the inward sides of the end plates, are made to arch inwards to insure the ball can only roll in said configuration in contact with both cylinder and one of the plates. As ball 13 rolls, electrical contact with wall 17 is intermittent, owing to the previously mentioned variations in contact resistance. On an oscilloscope the voltage measured between the positive and negative poles which are shown in FIG. 1 appear as a sequence of sharp rises and falls, and in turn can be used to generate a sequence of rectangular voltage pulses pre-designed in magnitude and time duration. These pulses can then be integrated over time. If motion does not continue, the voltage can be arranged to be dissipated by leakage which effectively prevents the integral from reaching a value that will activate an alarm. If motion persists, however, a tiny radio transmitter in an electronic circuit means (FIG. 2) activated sending a signal tone to a common household radio receiver located nearby.

As shown In FIG. 2, the electronic circuit means functions with a very small number of discrete components, operating from a single 3 volt DC watch battery. The circuit shown in FIG. 2 is designed with the limitations of power and size dictated by its intended place of use. Thus, all active components are low power CMOS devices or FETs.

Figure 2A:
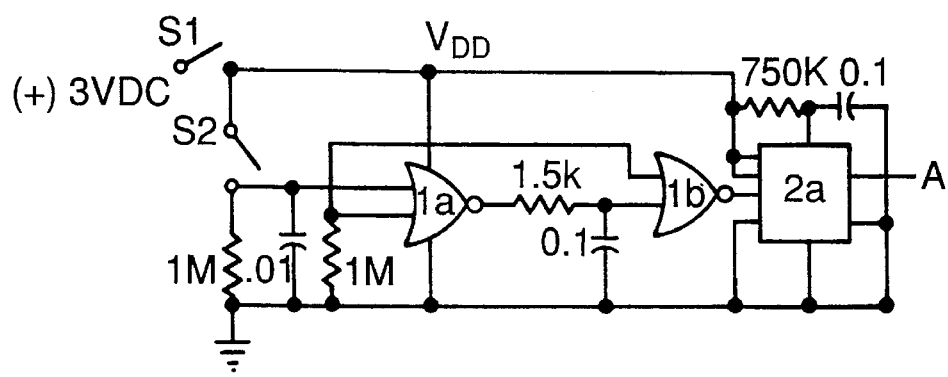
FIG. 2 (comprised of FIGS. 2A, 2B and 2C), shows a circuit diagram of the present invention illustrating the preferred embodiment as it is designed for use with an epileptic child needing overnight motion supervision. Its FIG. 2A section shows an edge detector stage which feeds into FIG. 2B summing integrator to close a latch stage, which in turn activates an alarm stage in FIG. 2C.
Figure 2B:
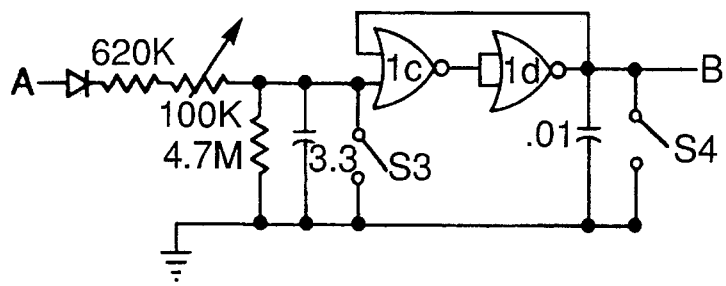
Figure 2C:
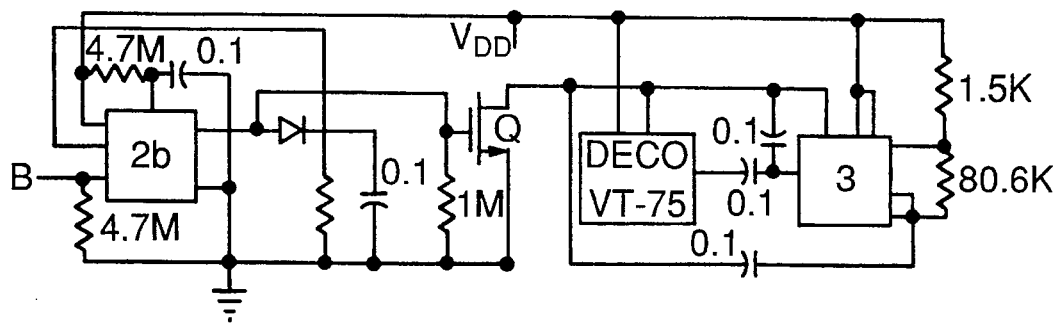

The circuit shown in FIG. 2 can be divided into four primary functions. These are: an edge detector and signal conditioner (FIG. 2A); an integrator with a latch (FIG. 2B); and an alarm mechanism. (FIG.2C) S2 represents element 11 of FIG. 1, whereas switch S1 represents merely a power-on switch. The edge detector is able to detect a sudden rise, or a sudden fall, in the voltage level (the "spikes"). Either change tends to indicate a motion made by the patient. In response to the above detections, of either an up or a down-going spike, the conditioner circuit will generate positive going pulses, all of equal height (amplitude) and of equal width, irregardless of the spike's polarity, amplitude, or (short) duration. If motion changes occur during the period of one of these pulses, such changes will not be acted upon. The count of the number of the square pulses is an indication of the number of motions that were made.

The edge detector comprises two coupled NOR gates $a$ and $1b$, as shown In FIG. 2, because the state of switch 11 when it is at rest is not known, nor can it be known if it is to operate over universal conditions. A non-retriggerable monostable multivibrator $2a$ conditions the signal produced by the edge detector to match the characteristics of switch 11 to the motions of interest. As has been noted, the switch 11 and the circuit of FIG. 2 ensure that the system will be less sensitive to large motions than it is to the smaller vibrations associated with 'hard shiver' epilepsy seizures.

The output of the monostable multivibrator $2a$ at A is fed to an Integrator A–B, where the pulses are summed and trigger a latch (shown by the remaining NOR gates $1c$ and $1d$ if the CMOS logic threshold is exceeded. Note also that the control voltage continuously decays through a bleeder resistor 4.7M will eventually drop to zero at Vss' when the system is at rest.

The output B of the latch enables an astable multivibrator designed from the second monostable multivibrator $2b$. The output of this astable multivibrator $2b$ is designed to pulse a VMOS power FET and permit a 3 volt battery to operate a transmitter DECO VT-75 at controlled bursts of relatively high current drain. The frequency of oscillation used as an input to the transmitter is derived from a 555 low power timer 3 configured to oscillate at about 600 Hz. The 555 is also enabled by the VMOS power FET. Pulsing both the transmitter and the 555 minimize current drain and limit the standby current to about 4 micro amps.

As shown In FIG. 1, the motion sensor of the present Invention is designed for attachment to a person who is susceptible to epileptic seizures, particularly of the forms of epilepsy which are life threatening, such as those which may be characterized by a 'hard shiver'. The watch strap in FIG. 1 is a means for attaching the sensor or the entire monitor to the patient, on a wrist, for example, or on a leg. In some cases the monitor may be worn as a belt. A buckle is shown in FIG. 1, but other attachment means can be used such as Velcro® fasteners and the like.

The procedure to use the sensor includes the following steps. The sensor is shaken sufficiently to trigger the radio alarm. The radio is tuned until the alarm tone is heard. The reset switches S3 and S4 are then momentarily closed on the sensor, stopping the alarm. The sensitivity of the sensor is then adjusted so that the alarm sounds in response to motion that has persisted for a length of time determined by the operator, usually the parent. The reset switches S3 and S4 are again closed momentarily and the sensor is now in its ready to use state.

In applying the motion sensor to an epileptic child, it is desirable that occasional movement not indicative of the seizure not trigger the alarm. The sensor sensitivity effectively selects a time period during which motion must be quasi-continuous for the alarm to be triggered. In addition, the switch design is such that it is more sensitive to small motions than to large since the rolling sphere breaks contact with either the end plate or the cylindrical wall with virtually every small movement of the sensor. Of course, the sensitivity can be adjusted or set at various settings depending upon the degree of sensitivity needed and the particular application of interest. When the motion sensor is applied to situations in which any or all motion is of interest, the sensitivity can be set at the maximum setting. The device may also be useful for monitoring brain injured persons in a health care facility it is suggested.

While particular embodiments of the present invention have been illustrated and described herein, it is not intended that these illustrations and descriptions limit the invention. Changes and modifications may be made herein without departing from the scope and spirit of the following claims.

We claim:

1. A device for attachment to a human patient for automatically monitoring said patient for occurence of an attack resulting from the medical condition of status epilepticus, wherein even barely perceptible shaking movements of the patient in any direction, or at any angle, may be sensed, and the number of such movements are being monitored, said device comprising: an electrically conductive hollow cylinder means, capped at each end respectively by an electrically conductive circular plate which is electrically insulated from said cylinder means, whereby said plates and said cylinder means are connected through an electronic circuit means to a direct current voltage source such that both plates are of the same polarity but opposite to the the polarity of said cylinder means, an electrically conductive ball placed within said cylinder being free to roll, said ball being able to establish a closed electrical path at either end of the cylinder means through contacting the interior surface of either one of said end circular plates while also contacting the interior surface of said cylinder means, whereby changes in electrical resistance over a multitude of contacted points of the interior surfaces of the cylinder means and of the circular plate contacted are detected in said electronic circuit means as a series of electrical current makes and breaks, and as changes in the level of electrical current flow through said electronic circuit means as the ball moves while making such closed electrical path, through even slight movements of said ball caused by patient movement.

2. The device as in claim 1 whereby detection in said electronic circuit means of shaking resulting from status epilepticus causes an alarm to be sounded.

3. The device as in claim 2 wherein said electronic circuit means includes an edge detector and conditioner circuit means for generating a sequence of voltage pulses of equal time duration and of equal amplitude in response to said electrical current makes and breaks, said edge detector and conditioner circuit means including a pair of coupled NOR gates to detect the make and break signals, and a non-retriggerable monostable multivibrator to condition the make and break signals into said pulses.

4. The device as in claim 3 wherein said electronic circuit means further includes a means for integrating said voltage pulses over a predetermined length of time to form an integrated value signal, said means for integrating including threshold means for initiating an alarm signal when the integrated value signal exceeds a preselected amount.

5. The device of claim 4, wherein said device further includes transmitter means to produce a transmitted radio signal upon receipt of said alarm signal, said radio signal being received by a conventional radio.

* * * * *